United States Patent
Hall et al.

(10) Patent No.: US 10,060,111 B2
(45) Date of Patent: Aug. 28, 2018

(54) TOILET WITH AIR SAMPLING EXHAUST

(71) Applicants: David R. Hall, Provo, UT (US); Dan Allen, Springville, UT (US); Ben Swenson, Lehi, UT (US); Jared Reynolds, Pleasant Grove, UT (US); Terrece Pearman, Draper, UT (US)

(72) Inventors: David R. Hall, Provo, UT (US); Dan Allen, Springville, UT (US); Ben Swenson, Lehi, UT (US); Jared Reynolds, Pleasant Grove, UT (US); Terrece Pearman, Draper, UT (US)

( * ) Notice: Subject to any disclaimer, the term of this patent is extended or adjusted under 35 U.S.C. 154(b) by 0 days.

(21) Appl. No.: 15/338,861

(22) Filed: Oct. 31, 2016

(65) Prior Publication Data

US 2017/0204595 A1    Jul. 20, 2017

Related U.S. Application Data

(60) Provisional application No. 62/280,140, filed on Jan. 19, 2016.

(51) Int. Cl.
| | |
|---|---|
| *E03D 9/04* | (2006.01) |
| *E03D 9/052* | (2006.01) |
| *F16K 31/06* | (2006.01) |
| *G01N 33/00* | (2006.01) |

(52) U.S. Cl.
CPC .......... *E03D 9/052* (2013.01); *F16K 31/0655* (2013.01); *G01N 33/0047* (2013.01)

(58) Field of Classification Search
CPC .. E03D 9/04; E03D 9/05; E03D 9/052; F16K 31/0655; G01N 33/0047

USPC ............................................................. 4/213
See application file for complete search history.

(56) References Cited

U.S. PATENT DOCUMENTS

| | | | | |
|---|---|---|---|---|
| 908,393 | A * | 12/1908 | Cline | E03D 9/052 |
| | | | | 4/214 |
| 1,894,846 | A * | 1/1933 | Pennoyer | E03D 9/052 |
| | | | | 4/213 |
| 1,972,774 | A * | 9/1934 | Hartwell | E03D 9/052 |
| | | | | 4/213 |
| 2,148,896 | A * | 2/1939 | Bertrand | E03D 9/052 |
| | | | | 4/215 |
| 2,575,778 | A * | 11/1951 | Wilson | E03D 9/052 |
| | | | | 4/213 |
| 2,677,830 | A * | 5/1954 | Allen | A47K 13/26 |
| | | | | 4/213 |

(Continued)

*Primary Examiner* — Benjamin R Shaw

(57) ABSTRACT

The present invention is directed to a device that measures volatile organic compounds (VOCs) emitted by an individual's urine, feces or present in flatulence for use in assessing the individual's health. The device may be part of a toilet. The device includes a gas sensor that measures VOCs in the air within the toilet bowl after waste is deposited therein. The device includes a manifold that keeps air from the toilet bowl separate from water and waste in the toilet bowl until the gas sensor has collected readings. Then the manifold combines the air, water, and waste before depositing the material into the sewer system. The gas sensor may be connected to a processor that analyses the gas sensor readings, provides a report of the analyzed data, and transmits the data to a network. A healthcare provider may download the data from the network to assess the individual's health.

15 Claims, 9 Drawing Sheets

(56) References Cited

U.S. PATENT DOCUMENTS

| | | | | |
|---|---|---|---|---|
| 3,703,010 A | * | 11/1972 | Russell | E03D 9/052 4/216 |
| 4,365,361 A | * | 12/1982 | Sanstrom | E03D 9/052 4/213 |
| 4,933,996 A | * | 6/1990 | Sowards | E03D 9/052 4/209 R |
| 5,201,079 A | * | 4/1993 | Sowards | E03D 9/052 4/213 |
| 5,288,306 A | * | 2/1994 | Aibe | B01D 53/02 95/141 |
| 5,361,422 A | * | 11/1994 | Vincent | E03D 9/05 4/213 |
| 5,386,594 A | * | 2/1995 | Hilton | E03D 9/052 4/213 |
| 5,403,548 A | * | 4/1995 | Aibe | B01J 20/20 4/213 |
| 5,829,066 A | * | 11/1998 | Aibe | E03D 9/052 4/213 |
| 6,173,453 B1 | * | 1/2001 | Shahar | E03D 9/05 4/213 |
| 6,499,150 B1 | * | 12/2002 | Thompson | E03D 9/052 4/213 |
| 7,461,410 B1 | * | 12/2008 | Shaffer | E03D 9/05 4/209 R |
| 2006/0008918 A1 | * | 1/2006 | Probert | G01N 33/497 436/106 |
| 2006/0037127 A1 | * | 2/2006 | Chen | E03D 9/05 4/213 |
| 2006/0200897 A1 | * | 9/2006 | Taylor | E03D 9/052 4/216 |
| 2008/0216220 A1 | * | 9/2008 | Markaj | E03D 9/052 4/213 |
| 2009/0275852 A1 | * | 11/2009 | Oki | A61B 5/097 600/532 |
| 2011/0156715 A1 | * | 6/2011 | Groves | G01N 27/66 324/466 |
| 2012/0219462 A1 | * | 8/2012 | Nozaki | B01J 20/3483 422/122 |
| 2015/0074886 A1 | * | 3/2015 | Wu | E03D 9/052 4/213 |
| 2015/0107009 A1 | * | 4/2015 | Quick | E03D 9/052 4/348 |
| 2015/0211222 A1 | * | 7/2015 | Perotto | E03D 9/052 4/213 |

* cited by examiner

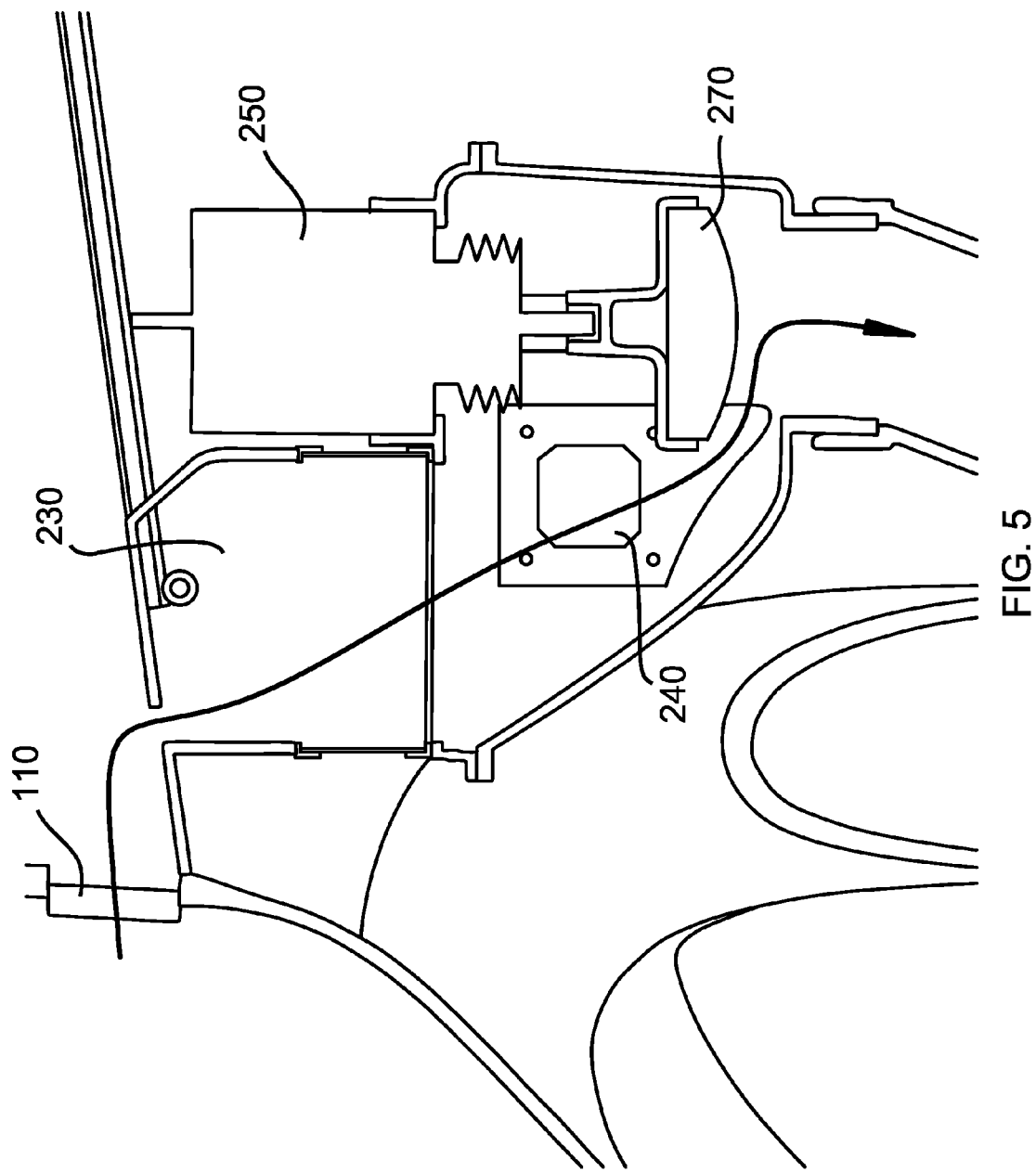

TOILET WITH AIR SAMPLING EXHAUST

CROSS-REFERENCE TO RELATED APPLICATIONS

This application claims priority to U.S. provisional patent application Ser. No. 62/280,140 filed on Jan. 19, 2016, the entire contents of which is hereby incorporated by reference.

BACKGROUND

Field of the Invention

This invention relates to toilets, and, in particular, toilets capable of analyzing the content of volatile organic compounds present in the air within the toilet bowl.

Background of the Invention

Urine, feces, and flatulence contain volatile organic compounds (VOCs), the composition of which varies depending on the physiological state of the individual. Knowledge of VOC profiles may provide useful information about an individual's health status and may aid in diagnosis of illness. For example, it has been reported that *Clostridium difficile*, *Campylobacter*, *Salmonella*, and *Cholera*, which are bacteria associated with different gastrointestinal infections, each have a unique VOC profile in fecal headspace samples. While analysis of urine and feces may be conducted in a clinical setting, a daily assessment of the components of an individual's waste is not typically feasible outside of a hospital. Analysis of VOCs emitted by waste is not a standard laboratory assay performed even in a healthcare facility.

A device which measures VOCs emitted by urine, feces, and flatulence is needed. In particular, a device which performs these measurements each time an individual uses the toilet so that multiple measurements are collected is needed.

SUMMARY

We disclose a novel device for measuring volatile organic compounds (VOCs) emitted from a user's waste or flatulence. The device may be included in a toilet. The device may include a fan or other device known in the art for moving air in a defined direction and an air sensor. The fan and air sensor may be connected to a vent within a toilet bowl. When a user deposits waste in the toilet bowl or emits flatulence into the air within the toilet bowl, the fan may direct the air within the toilet bowl toward the gas sensor. The toilet includes a hydraulic circuit which includes a P-trap. Unlike traditional toilets the P-trap may be part of a manifold. An air pipe may also be part of the manifold. Accordingly, the manifold separates air and water, the latter which may include waste, until after the gas sensor has measured the contents of the air. The contents of the manifold are then combined and deposited into the sewer system.

Some embodiments disclosed herein include a processor which performs tasks such as recording data from the gas sensor, combining this data with that collected from other sensors, and providing reports that may be relevant to a user's health status. The data may be uploaded to a network from which a user's healthcare provider may download the data for use in diagnosis or other assessment of the user's health status.

BRIEF DESCRIPTION OF THE DRAWINGS

FIG. 5 is a cross sectional drawing of a toilet as disclosed herein illustrating the pathway of air through the device disclosed herein.

DETAILED DESCRIPTION

Definitions

Toilet, as used herein, means a device that may be used to collect one or more biological waste products excreted by a user.

User, as used herein, means a human or animal that deposits bodily waste into an embodiment of the toilet disclosed herein.

Water, as used herein, means water without significant additives or water with waste added to it. For example, water, as used herein, may include urine, feces (either liquid or solid), vomit or other material added to the toilet bowl by a user.

Waste, as used herein, means urine, feces (either liquid or solid), vomit, or other biological products that a user may deposit into a toilet bowl.

Reference in the specification to "one embodiment" or "an embodiment" means that a particular feature, structure, or characteristic described in connection with the embodiment is included in at least one embodiment, but is not a requirement that such feature, structure or characteristic be present in any particular embodiment unless expressly set forth in the claims as being present. The appearances of the phrase "in one embodiment" in various places may not necessarily limit the inclusion of a particular element of the invention to a single embodiment, rather the element may be included in other or all embodiments discussed herein.

Disclosed herein is a toilet capable of measuring and analyzing volatile organic compounds (VOCs) that may be present in the air within a toilet bowl upon use. Specifically, the disclosed toilet comprises an air vent which may be positioned within the toilet bowl. The air vent leads to a gas analyzer and a fan or other air-moving device directs the air from the toilet bowl, through the vent, and towards the gas analyzer. The toilet includes a mechanism for keeping the gas that is directed to the gas analyzer separate from the air in the sewer system during analysis, then depositing the air into the sewer system after analysis. Information about the VOCs that are emitted from a user's waste or flatulence may be used to extrapolate information about a user's health status.

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
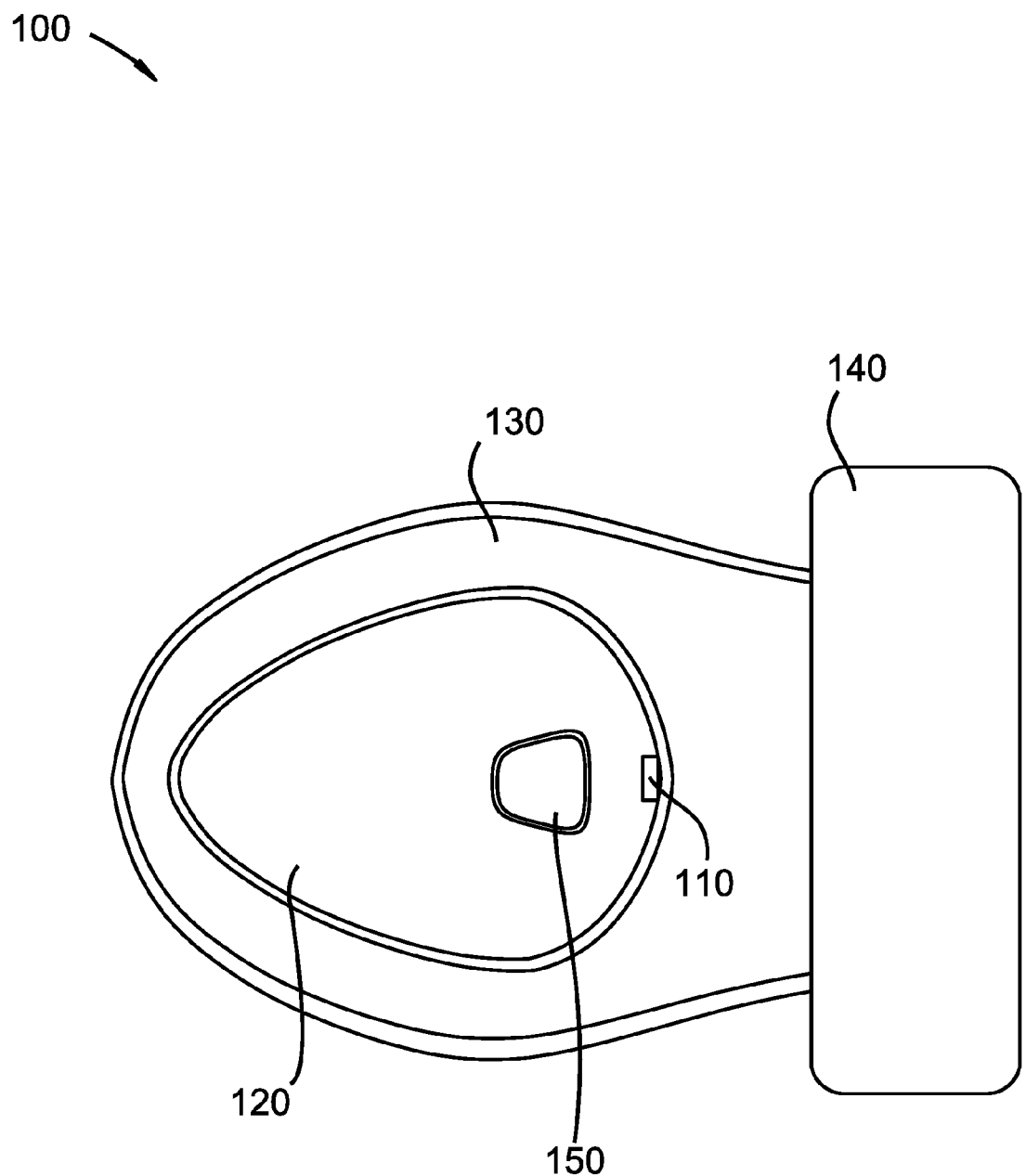
FIG. 1 is a schematic illustration of a toilet illustrating a vent leading to a gas sensor.

Referring to FIG. 1, toilet 100 is illustrated as a view from above a toilet according to an embodiment of the invention. Like conventional toilets, toilet 100 includes toilet bowl 120, rim 130, tank 140, and waste port 150 through which water travels into the P-trap and toward the sewer system. In addition, toilet 100 includes air vent 110. Air vent 110 may an opening within the toilet bowl and above the water line through which air from the toilet bowl may travel for analysis.

Figure 2:
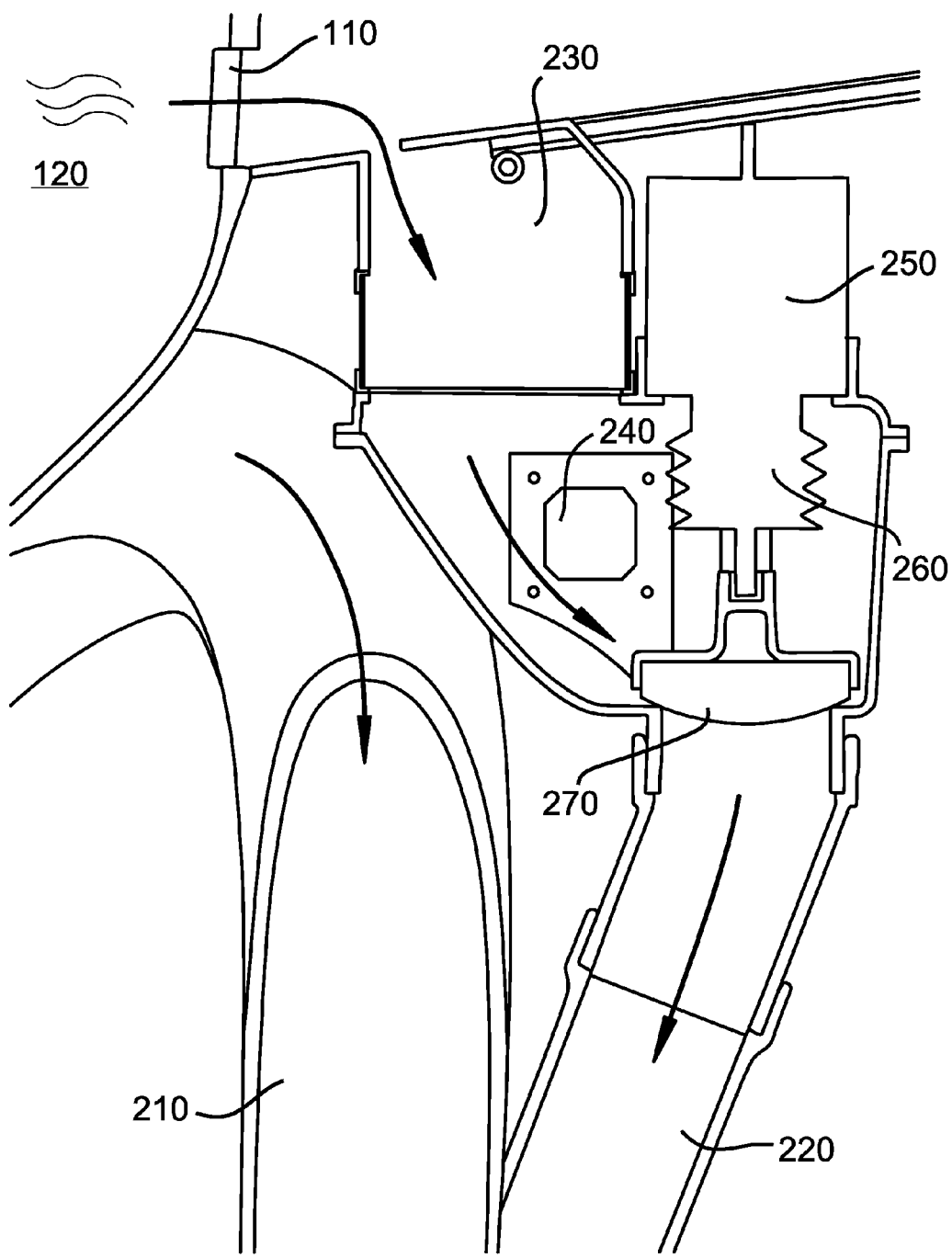
FIG. 2 is a cross section of the gas sensor and air management system according to an embodiment of the invention.

FIG. 2 is a cross-section of a device for analyzing air within a toilet bowl according to an embodiment of the invention. FIG. 2 shows air vent 110 as first presented in FIG. 1. Air vent 110 is positioned within the toilet bowl above the water line to prevent excessive amounts of water from entering the air vent. Air vent 110 leads from toilet bowl 120 into air pipe 220 which, in this embodiment, is part of a bifurcated manifold. In other embodiments, the manifold may include more than two extensions. Air pipe 220 connects air vent 110 with an output port that leads into a sewer pipe. Fan 230 is located within air pipe 220 and, when actuated, draws air from toilet bowl 120, through air vent 110, and into air pipe 220. Wavy lines shown within toilet bowl 120 represent air moving toward air vent 110 and arrows moving from air vent 110 through air pipe 220 indicate the direction of air movement in response to fan 230. Note that fan 230 may be positioned in other regions of air pipe 220. In addition, other devices that move air are within the scope of the invention. Moving further along air pipe 220, gas sensor 240 is shown. Air is drawn past gas sensor 240 which detects the types and amounts of VOCs in the air. Beyond gas sensor 240 is shown piston 270 which is connected to solenoid 260. Solenoid 260 is connected to base 250.

Note that the upper section of air pipe 220 is wider than the lower section. The width of piston 270 is approximately the same as or slightly less than the width of the lower section of air pipe 220 such that piston 270 forms an air seal when in a lowered position. In this lowered position, gases coming from the sewer system are unable to pass through air pipe 220 into the upper section. This has two functions: first, to prevent toxic sewer gases from bypassing the water seal and reaching the atmosphere outside of the toilet and second, to prevent gases other than those emitted by a user's waste or flatulence from creating background signal when gas sensor 240 is in use.

In contrast, the upper section of air pipe 220 is wider than the width of piston 270 such that when piston 270 is in an elevated position as occurs during use of the toilet, there is no seal blocking the movement of air through air pipe 220. Because fan 230 directs air downward from air vent 110 past piston 270 and toward the sewer pipe, air from toilet bowl 120 goes through air pipe 220 but not in the reverse direction up from the sewer toward toilet bowl 120.

Piston 270, solenoid 260, and base 250 form a valve. However, one of skill in the art will understand that other valves may be used in place of that illustrated in the Figures herein. Furthermore, the valve may be actuatable by a variety of means including, but not limited to, pneumatic, magnetic, and electrical means.

P-trap 210 is the second piece of the bifurcated manifold. As in conventional toilets, toilet water and waste travel from toilet bowl 120 through P-trap 210 toward the sewer pipe in the direction indicated by the arrows. Thus, the bifurcated manifold comprises two separate pipes, one for air and one for water and waste.

Figure 3:
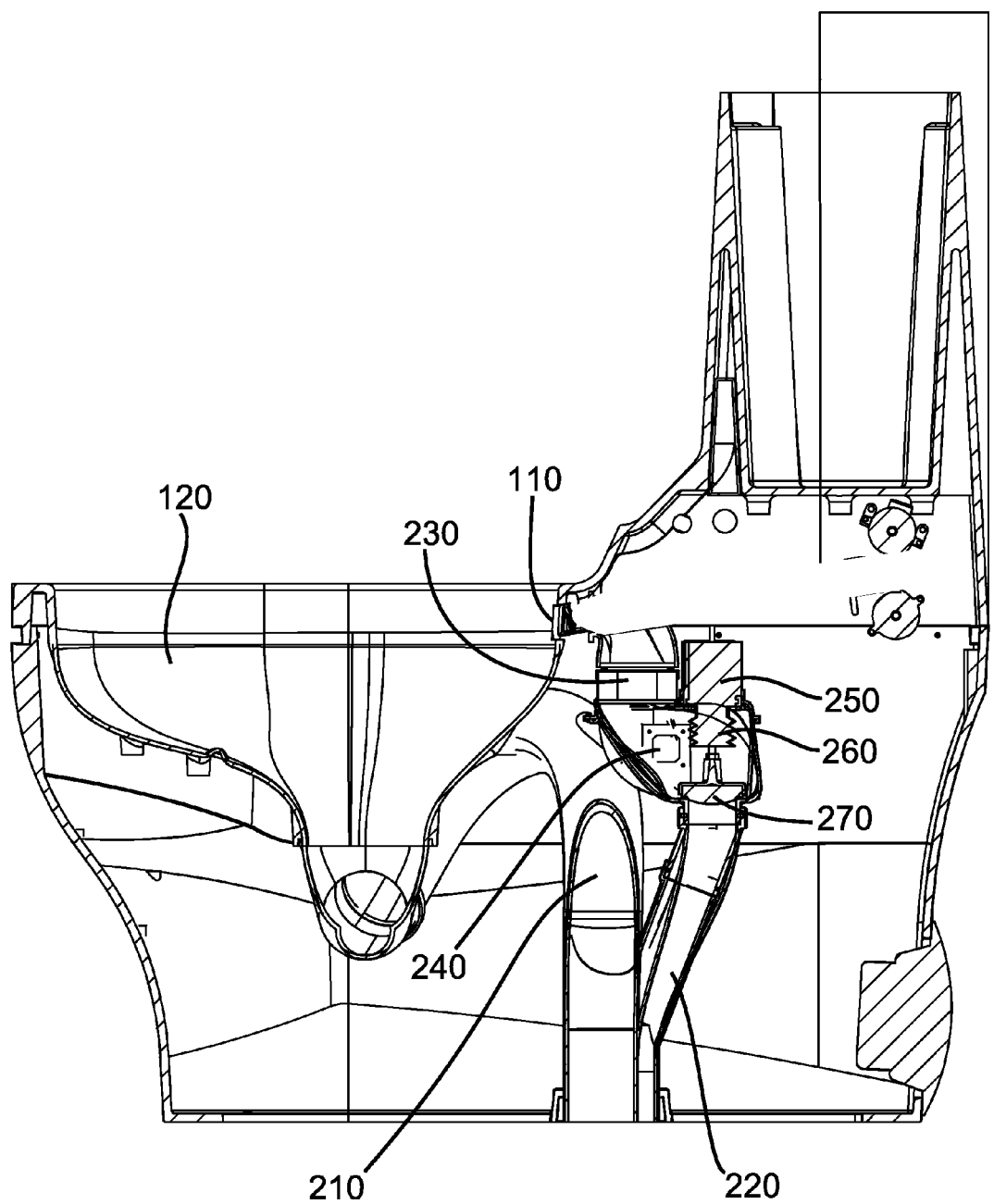
FIG. 3 is a cross section of a toilet illustrating an embodiment of the gas sensor and air management system as it may be included within a toilet.

FIG. 3 shows the device of FIG. 2 within a toilet. P-trap 210 connects to toilet bowl 120 below the water line while air pipe 220 connects to air vent 110 above the water line. P-trap 210 and air pipe 220 come together at their lower ends and, together, form a bifurcated manifold. The manifold connects to a sewer pipe at the bottom of the manifold through an output port.

Figure 4A:
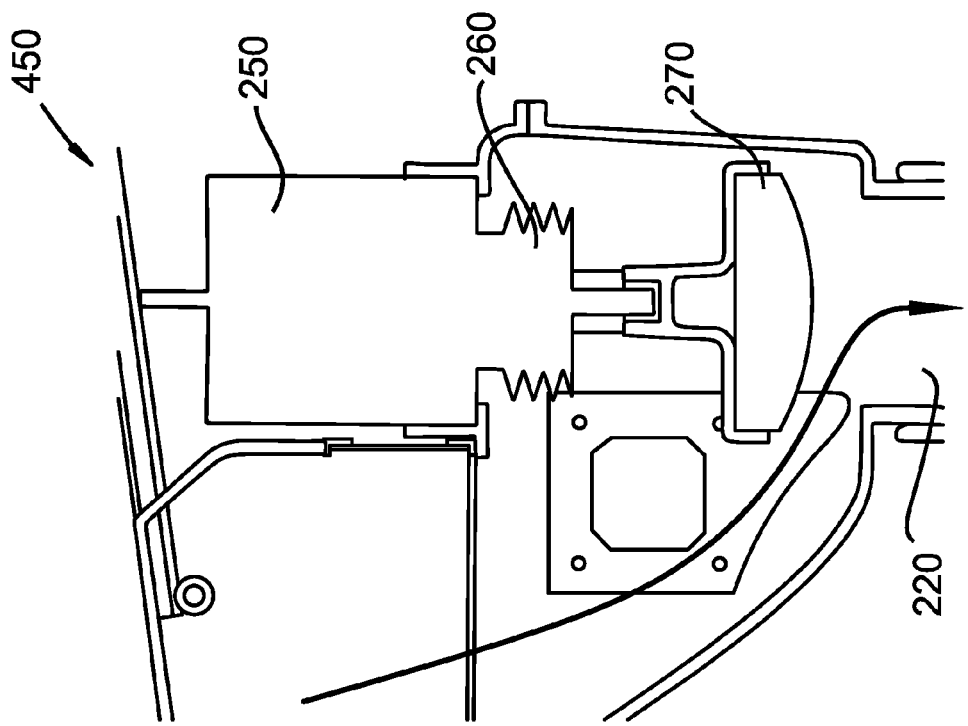
FIG. 4A is a schematic drawing illustrating a piston as a part of a valve within the disclosed device in its downward position creating an air seal.
Figure 4B:
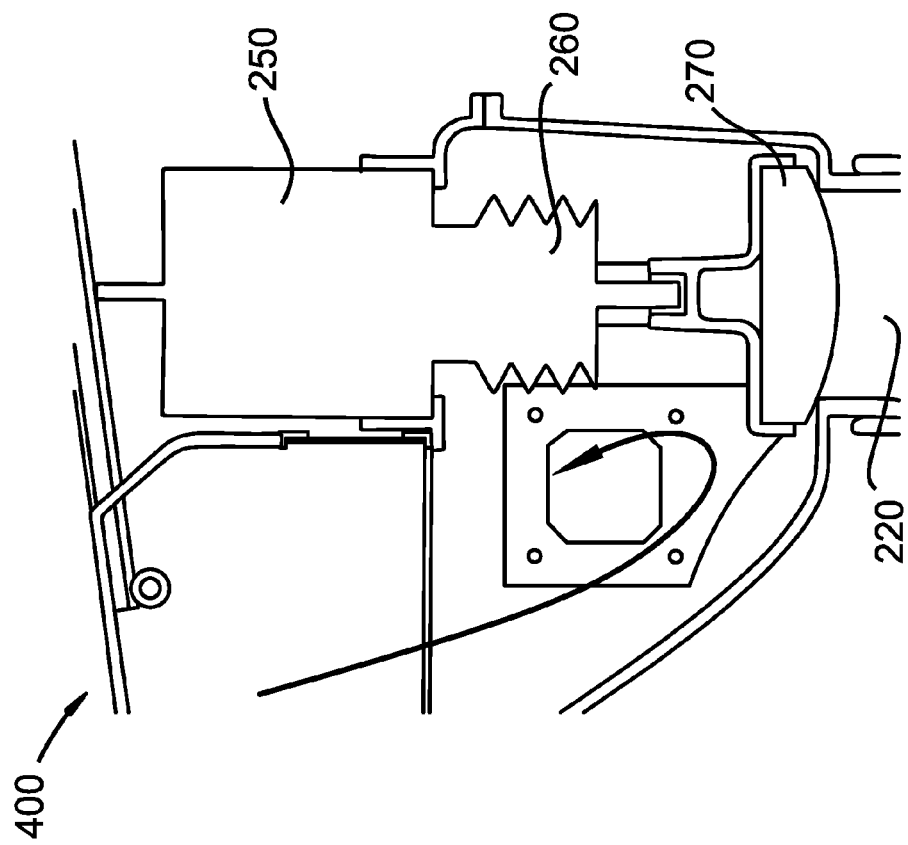
FIG. 4B is a schematic drawing illustrating the piston of FIG. 4A in its raised position which removes the air seal.

FIGS. 4A and 4B illustrate piston 270 raising to allow air to pass through air pipe 220 and lowering to create an air seal. FIG. 4A shows the piston in position 400 in which solenoid 260 has extended and piston 270 is lowered. Piston 270 is approximately the width of the lower end of air pipe 220. Because of the air seal, air is unable to continue through air pipe 220 from the upper end to the lower end. Likewise, gases that may come up from the sewer through air pipe 220 are also unable to move past the air seal.

FIG. 4B illustrates the piston in position 450 in which solenoid 260 is compressed and piston 270 is raised. In position 450, piston 270 is in the upper section of air pipe 220 which is wider than piston 270. There is no air seal preventing air from traveling through air pipe 220 as illustrated by the arrow. The arrow shows air moving only in the direction of the narrow end of air pipe. When piston 270 is in raised position 260, fan 230 directs air in the direction of the sewer pipe and away from air vent 110.

FIG. 5 shows piston 270 in position 450 as shown in FIG. 4B within a toilet. Piston 270 is raised into the wider, upper section of air pipe 220 so that there is no air seal to prevent air from moving through air pipe 220. Fan 230 is directs air from toilet bowl 120 through air vent 110 and through air pipe 220. The air passes gas sensor 240 which may take a reading of the contents of the air.

Figure 6:
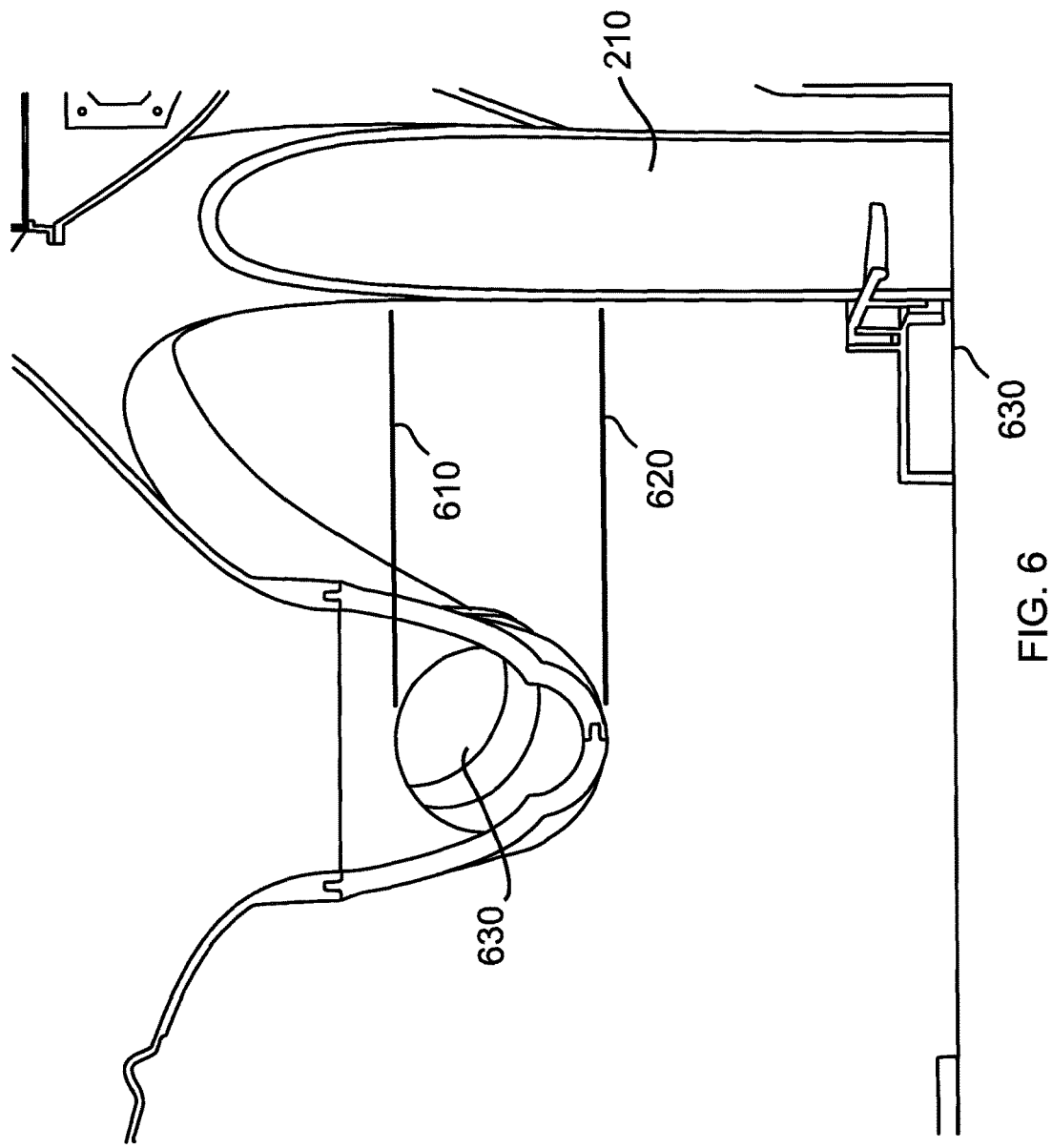
FIG. 6 illustrates multiple points at which the bifurcations of the manifold may intersect.

As discussed above, the manifold may be bifurcated and include an air pipe which transmits air and a P-trap which transfers water and waste. In this embodiment, the air pipe and P-trap come together to deposit their contents into a sewer pipe through an output port. The point at which the bifurcated manifold comes together to join the two pipes is preferably low enough to siphon the liquid contents of the toilet bowl into the P-trap when the toilet is flushed. FIG. 6 shows a cross section of P-trap 210 connected to a toilet bowl. Line 610 is level with the top of waste port 630. If P-trap 210 and air pipe 220 intersect above the level shown by line 610, P-trap 210 may not siphon the water and waste from the toilet bowl into P-trap 210. Line 620 is level with the bottom of waste port 150. In some embodiments, the bifurcated manifold intersects at the level of line 620. This embodiment will allow the contents of the toilet bowl to siphon into P-trap 210 upon flushing. In some embodiments, the bifurcated manifold intersects at point 630 which is the lowest point before the P-trap intersects with the sewer pipe. This embodiment will also allow the contents of the toilet bowl to siphon into P-trap 210 upon flushing.

Some embodiments include a processor and the processor may further include a program for analyzing gas sensor readings. The processor may be connected to one or more of the fan, the gas sensor, and the piston. In some embodiments, the processor actuates the fan when receiving a reading from the gas sensor. The purpose of actuating the fan when the gas sensor detects VOCs may be to actuate the system to take a reading because a user has deposited waste into the toilet or to prevent the ingress of sewer gas that may have leaked past the piston's air seal. The program may analyze the reading from the gas sensor and identify that the gas is sewer gas based on its contents. Then the program may report the ingress.

Figure 7:
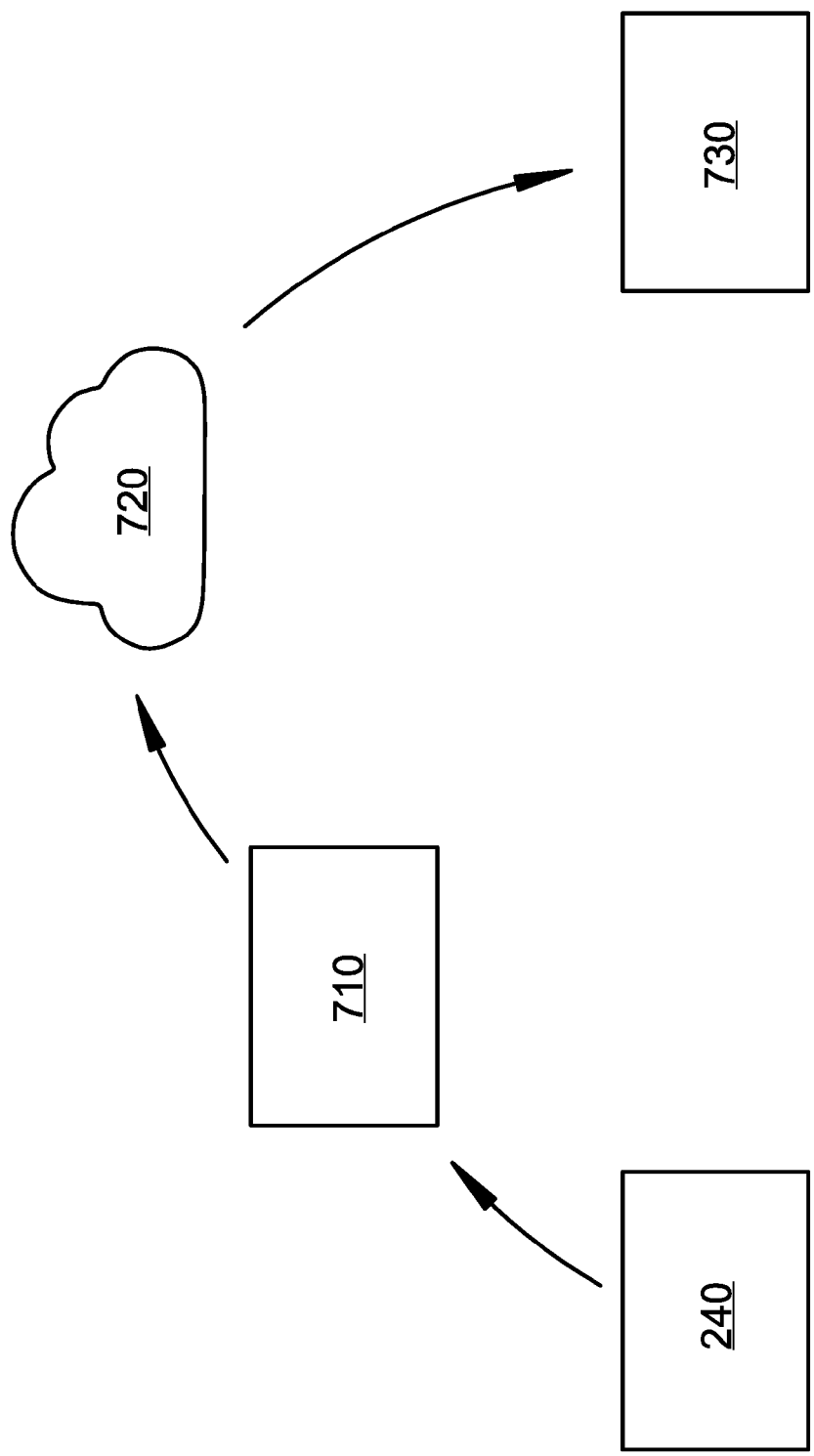
FIG. 7 is a schematic drawing illustrating a method of using the disclosed gas sensing device including uploading the data to a network.

FIG. 7 illustrates an embodiment in which gas sensor 240 is connected to processor 710. In some embodiments, processor 710 may transmit readings from gas sensor 710 and analysis thereof conducted by the program to network 720. In this embodiment, the device within the toilet may include a computer network port. Third party processors, including processor 730 may download the data from network 720. Processor 730 may be a computer or patient database owned by the user's healthcare provider. In some embodiments, the program produces a report that includes information about a user's health status based, at least in part, on the analysis of the gas sensor readings taken when the user deposited waste into the toilet. For example, the program may review the gas sensor readings and determine if they fit the unique profile that is associated with *Clostridium difficile, Campylobacter, Salmonella,* and *Cholera*, which are bacteria associated with different gastrointestinal infections.

Figure 8:
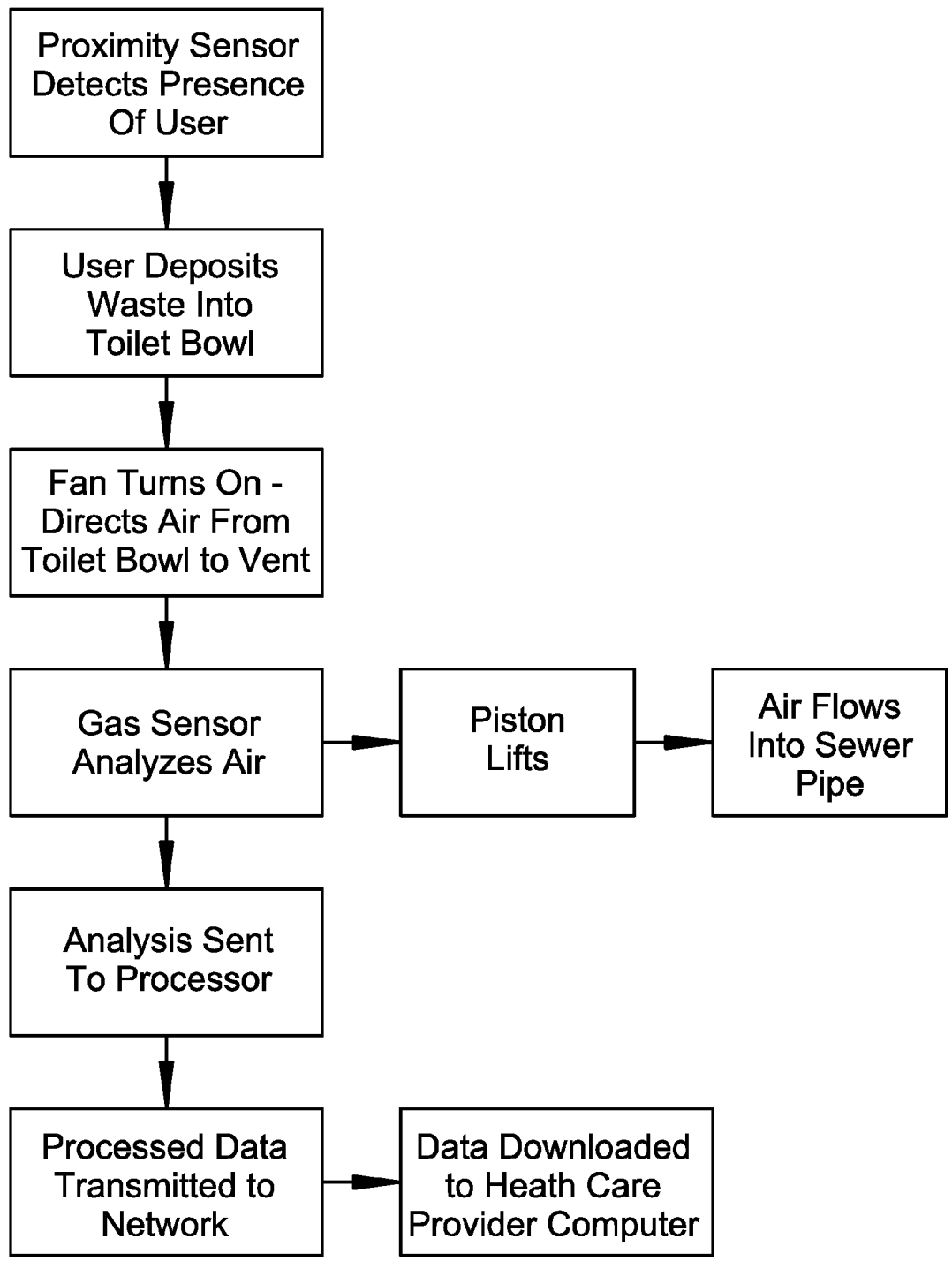
FIG. 8 is a flow chart illustrating an embodiment of a method of using the disclosed gas sensing device as it may be used within a toilet.

FIG. 8 is a flow chart illustrating an embodiment of a method of using the toilet disclosed herein. In this embodiment, the toilet includes a proximity sensor that detects the presence of a user. The user then deposits waste into the toilet bowl. The processor, which may be connected to the proximity sensor and respond to a signal from the proximity sensor, actuates the fan. The fan directs air from the toilet bowl to the air vent and into the air pipe. The gas sensor detects VOCs that may be present in the air coming from the toilet bowl. In some embodiments, the processor may signal the piston to lift, removing the air seal so that the air can continue through the manifold into the sewer pipe. Additionally, the gas sensor may be connected to the processor. A program that is within the processor may analyze signals collected by the gas sensor and transmit the processed data to a network using a computer network port. The user's healthcare provider may download the data to a local computer at a healthcare facility to use in diagnosing the user or otherwise assessing the user's health status.

Figure 9:
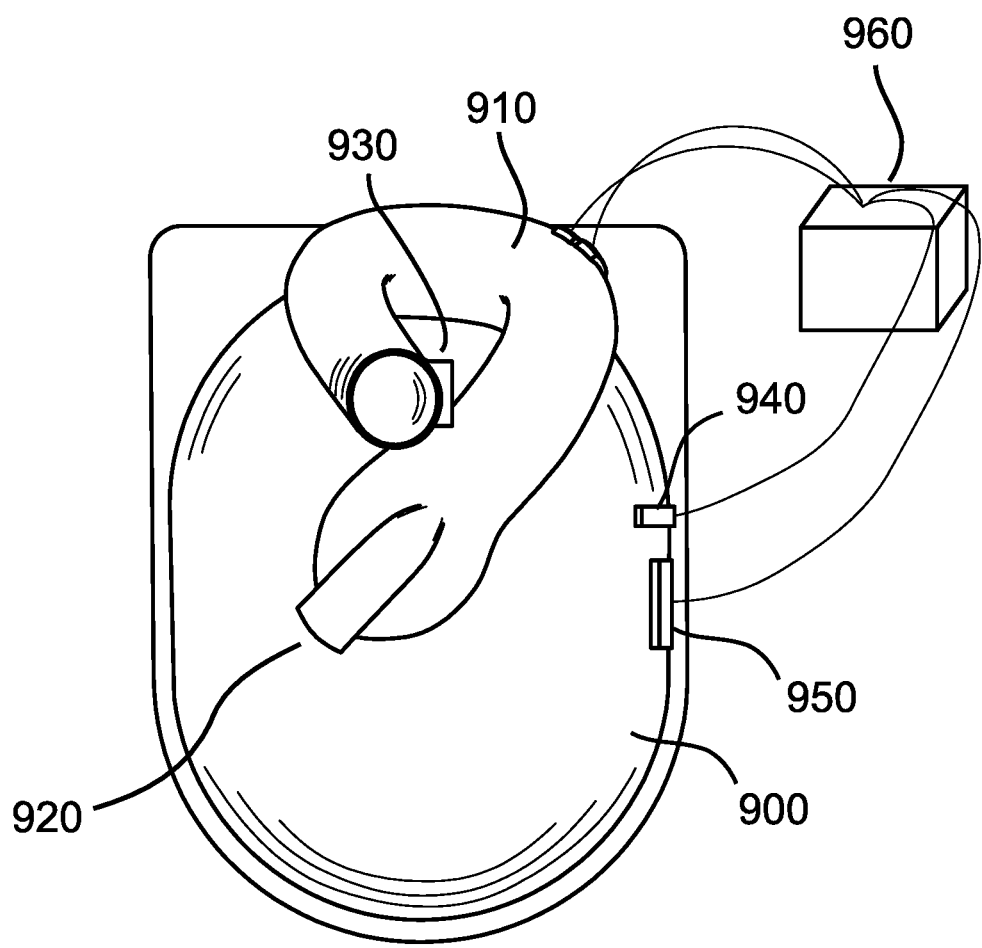
FIG. 9 is an embodiment of a toilet that includes other sensors in addition to the gas sensor, which may collect other metrics to combine with that of the gas sensor.

FIG. 9 illustrates an embodiment of a toilet that includes multiple sensors connected to processor 920. This embodiment includes a helical drain as disclosed in U.S. patent application Ser. No. 15/168,664 filed on May 31, 2016, which is hereby incorporated by reference in its entirety. The toilet includes capacitance sensors 940 and 950 which measure the flow through helical drain 910. Helical drain includes port 930. The toilet of FIG. 9 may further include the air vent, gas sensor, manifold, and other components of the gas analysis system disclosed herein. The air vent may be positioned within toilet bowl 900, connected to a gas sensor, and the gas sensor may be connected to processor 960. In other embodiments, the toilet may include other sensors that collect data that may be relevant to a user's health, particularly when combined with the data collected by the gas sensor.

There is thus disclosed a device that may be connected to or be part of a toilet to measure and analyze VOCs present in a user's waste and/or flatulence. This data may be used to assess the user's health status.

While specific embodiments have been described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

The invention claimed is:

1. A toilet for analyzing air within a toilet bowl, comprising:
    an air vent positioned within the toilet bowl above a standing water level;
    a manifold comprising:
        at least two separate pipes, the at least two separate pipes comprising:
            a first pipe comprising an air pipe;
                a gas sensor;
                a fan;
            a second pipe comprising a P-trap, the P-trap comprising an exit for conducting waste to a sewer pipe, and
        a waste port through which waste travels from the toilet bowl into the P-trap, and
        a capacitance sensor capable of measuring the flow through the second pipe.

2. The toilet of claim 1, wherein the air pipe further comprises an actuatable valve, wherein the valve gates the air flow through the manifold.

3. The toilet of claim 1, wherein the gas sensor detects volatile organic compounds.

4. The toilet of claim 1, further comprising a processor, wherein the processor comprises a program which analyzes gas sensor readings.

5. The toilet of claim 4, wherein the program produces data relevant to a user's health status.

6. The toilet of claim 4, wherein the processor is connected to and controls the fan, the gas sensor, and a valve.

7. The toilet of claim 6, wherein the processor actuates the fan when receiving a reading from the gas sensor.

8. The toilet of claim 4, wherein the program identifies sewer gas ingress into the manifold in response to a reading from the gas sensor.

9. A device for analyzing air within a toilet bowl, comprising:
    a manifold comprising at least two separate pipes, the at least two separate pipes comprising:
        a first pipe comprising an air pipe; the air pipe comprising:
            a gas sensor;
            a fan
        a second pipe comprising a P-trap, the P-trap comprising an exit for conducting waste to a sewer pipe, and
        a capacitance sensor capable of measuring the flow through the second pipe.

10. The device of claim 9, wherein the air pipe further comprises an actuatable valve, wherein the valve gates the air flow through the manifold.

11. The device of claim 9, wherein the gas sensor detects volatile organic compounds.

12. The device of claim 9, further comprising a processor, wherein the processor comprises a program which analyzes gas sensor readings.

13. The device of claim 12, wherein the program produces data relevant to a user's health status.

14. The device of claim 12, wherein the processor is connected to and controls the fan, the gas analyzer, and a valve.

15. The device of claim 14, wherein the processor actuates the fan when receiving a reading from the gas sensor.

* * * * *